(12) United States Patent
Singh (10) Patent No.: US 8,284,896 B2
(45) Date of Patent: Oct. 9, 2012

(54) MULTIVIEW X-RAY INSPECTION SYSTEM

(76) Inventor: Satpal Singh, Potomac, MD (US)

( * ) Notice: Subject to any disclaimer, the term of this patent is extended or adjusted under 35 U.S.C. 154(b) by 429 days.

(21) Appl. No.: 12/588,705

(22) Filed: Oct. 26, 2009

(65) Prior Publication Data

US 2011/0096903 A1 Apr. 28, 2011

(51) Int. Cl.
*G01N 23/04* (2006.01)
*G01T 1/00* (2006.01)
*H05G 1/08* (2006.01)

(52) U.S. Cl. .................. 378/62; 378/91; 378/41
(58) Field of Classification Search .......... 378/57, 378/62, 91, 41, 98.8; 250/336.1, 370.11
See application file for complete search history.

(56) References Cited

U.S. PATENT DOCUMENTS

| | | | |
|---|---|---|---|
| 6,853,707 B2 * | 2/2005 | Kerschner | 378/98.8 |
| 7,319,737 B2 | 1/2008 | Singh | |
| 2008/0152087 A1 * | 6/2008 | Tseng | 378/98.3 |

* cited by examiner

*Primary Examiner* — Irakli Kiknadze (57) ABSTRACT

A multiview x-ray scanning system for inspecting the 3D volume of an object has been presented. The method uses multiple x-ray sources and multiple x-ray beams. The object to be inspected is interposed in the trajectory of these beams and moved relative to these beams. The x-ray beams after passing through the object are detected by detectors that are interleaved to realize a compact design. In order that the interleaved detectors do not intersect, the location of detectors and sources is adjusted. Further, the design of detectors is such that they can be placed in close proximity to each other in order to realize a small footprint scanner having a high resolution.

11 Claims, 8 Drawing Sheets

MULTIVIEW X-RAY INSPECTION SYSTEM

BACKGROUND OF THE INVENTION

1. Field of the Invention

This invention describes a method of using x-rays to inspect an object or a parcel.

2. Description of the Related Art

Figure 1:
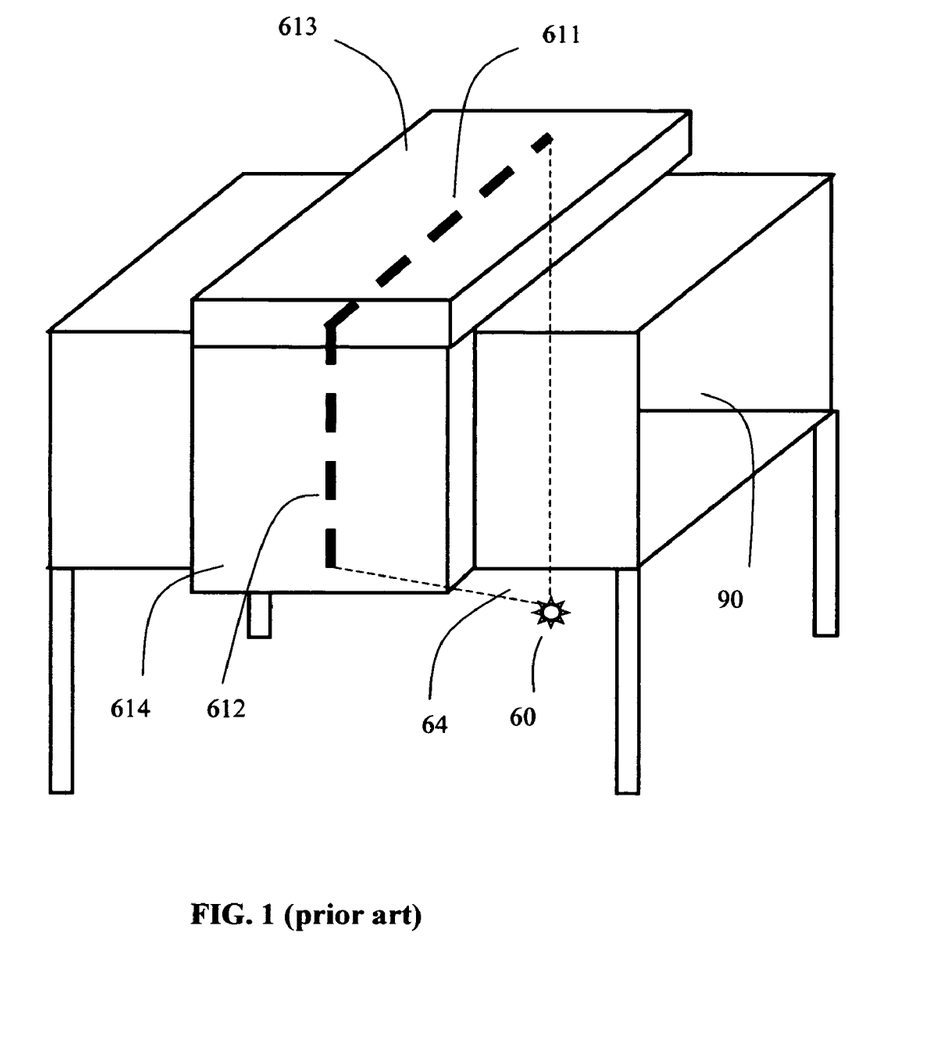
FIG. 1 shows the simplified view of a conventional x-ray scanner that produces 2D images.

X-ray scanners are used for baggage screening as at the airports, for inspection of parts in industrial use, for inspection of food cans by the food industry, and for any other inspection use. A simplified sketch of the conventional x-ray scanner is shown in FIG. 1. It uses a single x-ray source 60 which is placed below and to one side of the tunnel 90 as shown. A fan beam 64 from the source 60 then passes through the object or baggage inside the tunnel and impinges on the "L" shaped detectors 611 and 612 which are housed in detector electronic boxes 613 and 614 respectively. The image produced by such a scanner is 2D and lacks the detail needed to inspect the 3D volume of the object.

Therefore, to inspect the 3D volume, CT (Computed Tomography) or CAT (Computed Axial Tomography) systems are used. However these systems are not in wide use, as they are large, expensive, consume large power and need heavy duty cabling to be first installed in the room, and are not portable. Therefore to fill the gap between 2D scanners and the 3D CT systems, multi view systems have been developed.

Figure 2:
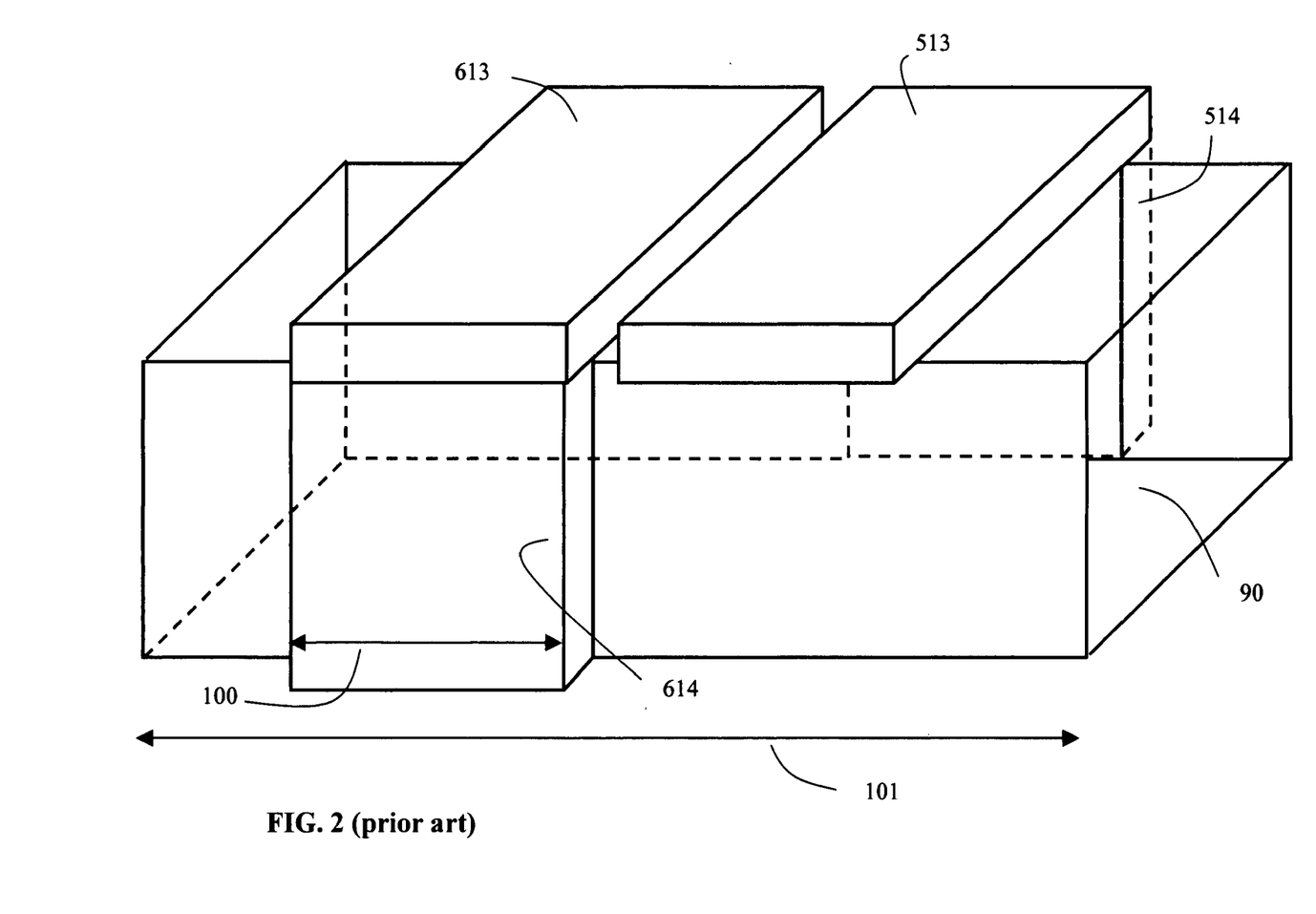
FIG. 2 shows the detector electronics box placement for a two view system.
Figure 3:
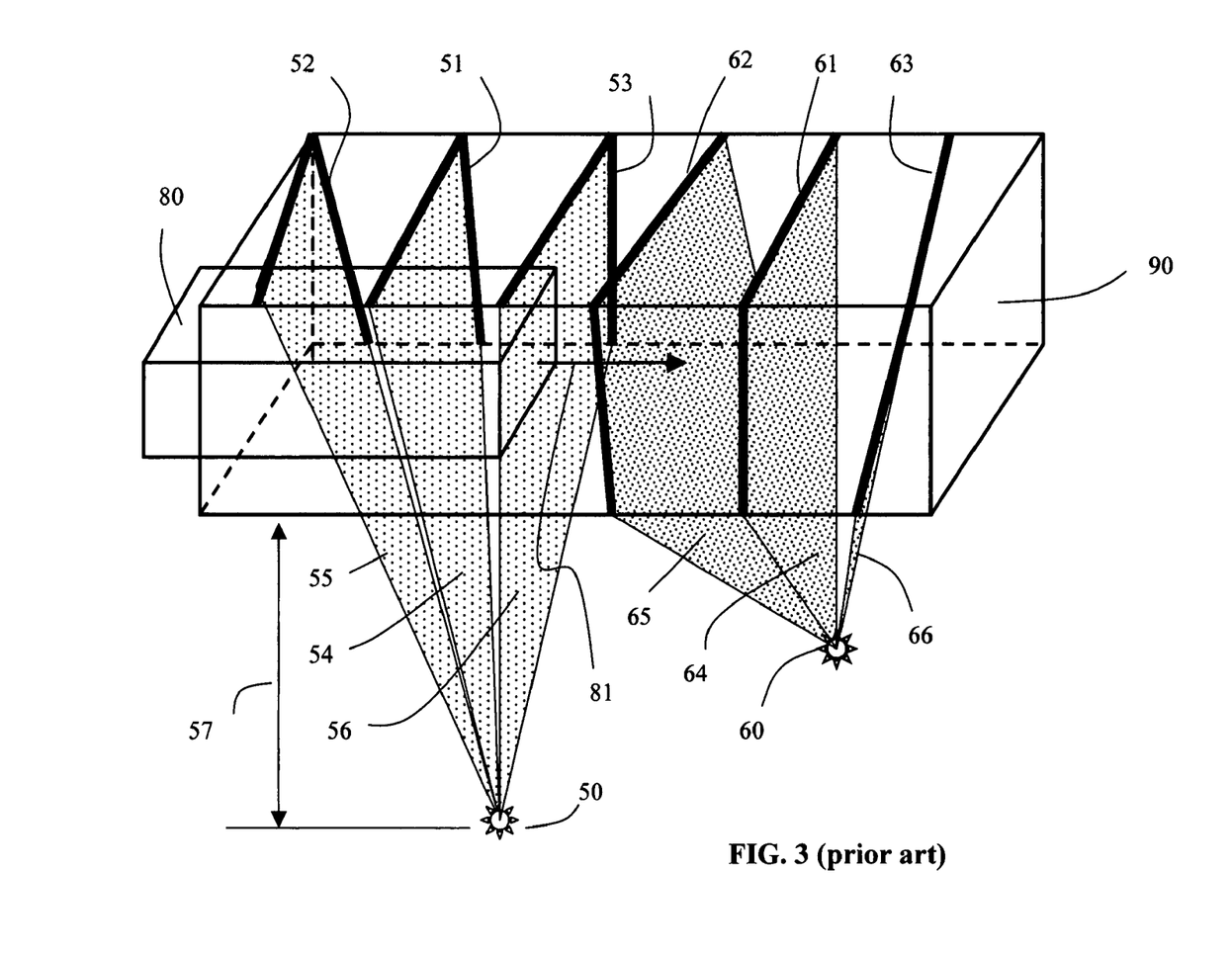
FIG. 3 shows a multi view system with 6 views and 2 sources as described in U.S. Pat. No. 7,319,737 B2 (Singh).

A simple multiview system with two views is shown in FIG. 2, and another system with two sources and six views as described in U.S. Pat. No. 7,319,737 B2 (Singh), is shown in FIG. 3. In FIG. 2, for the purposes of brevity, only the electronic boxes are shown. In comparison to FIG. 1, two additional boxes 513 and 514 are shown in FIG. 2. As is well known to a person skilled in the art, these would correspond to a second x-ray source placed on the other side of the tunnel across from the first source 50 of FIG. 1. The width 100 of the detector electronic boxes 613, 614, 513, 514 is usually in the range of twelve to fifteen inches. The addition of extra detector electronic boxes 513 and 514 makes the length 101 of the tunnel 90 longer.

Since the images produced from just two views is not sufficient to provide detailed information of a 3D object, more than two view systems have been developed. These multiview systems are three to five view systems. As would be apparent to a person skilled in the art, the addition of third or more views leads to adding more of detector electronic boxes to the system of FIG. 2. This leads to a large length of the tunnel which makes the system big. Such big systems are therefore not in use for the inspection of carry on baggage at check points in buildings or at airports where a small footprint is needed.

The problem becomes further worse for a system of FIG. 3 which uses slant beams that require detector electronic boxes to be positioned at oblique angles and where the separation between two adjacent detectors may be much less than twelve or fifteen inches needed to accommodate such wide electronic boxes that the current technology offers. The system of FIG. 3 uses two x-ray sources 50 and 60. The beams 54, 55 and 56 are associated with the first source 50, and are detected by detectors 51, 52 and 53 respectively. Likewise, the beams 64, 65 and 66 are associated with the second source 60, and are detected by detectors 61, 62 and 63 respectively. If such a system were to use wide electronic boxes of FIG. 1 or FIG. 2, the system of FIG. 3 would become very large and impractical for use in office buildings or where smaller footprint is needed.

The objects of this invention are therefore to overcome some of the above problems and are listed next.

OBJECTS OF THE INVENTION

It is, accordingly, an object of the invention to build a small size, multi view x-ray scanner system for the inspection of objects.

It is also an object of this invention to build a compact size scanner with more than two or three views so that a higher resolution and higher performance can be achieved that is needed for 3D inspection of an object, or for explosives detection as required for baggage scanners used at airports.

These and other objects will become apparent in the description that follows.

SUMMARY OF THE INVENTION

A x-ray scanning system for 3D inspection of an object is presented. The system described in this invention is a multiview system that is compact in size and hence would be useful as a check point security scanner for carry on baggage at airports, office buildings, etc. At present, there are no such compact multiview systems and most of the scanners in use today use the old technology that produces 2D images which are not good enough for detecting explosives or object of threats. In order to make a compact multiview system, the preferred embodiment of this invention uses two sources placed on two opposing sides of and below a tunnel through which the object or bag under inspection is conveyed. Each x-ray source emits three fan beams, one beam is perpendicular to the direction in which the bag or object is moved or conveyed through the tunnel, and two other beams are slanting, one towards and one away from the direction of conveyance of the object. In order to make the system compact, the two sources are located such that their beams interleave as they pass through the tunnel. Further, the detectors that detect these beams is such that the position of these detectors is interleaved. In order to realize such a system where the detectors for the various beam do not intersect, the angle of the beams and the vertical distance of the x-ray source beneath the tunnel are adjusted.

The existing multiview scanners are extremely large and not used at check points. When the size of the system is scaled down to make a small footprint scanner, the geometries and the spacing of detectors also scale down. This leads to a requirement that the detector electronic boxes needed to detect the various beams be placed with in a few inches of each other. To realize such a system, a new method of detector and electronic assembly is described wherein the electronic cards housing the preamplifiers are placed vertically with respect to the detector. This allows for very narrow detector electronic boxes of two to three inches width compared to the usual twelve to fifteen inches currently used.

There are several embodiments, objects and advantages to this invention that will be apparent to one skilled in the art. The accompanying figures and description herein should be considered illustrative only and not limiting or restricting the scope of invention, the scope being indicated by the claims.

DETAILED DESCRIPTION OF THE PREFERRED EMBODIMENTS

In describing the preferred embodiment and its alternatives, specific terminology will be used for the sake of clarity. However, the invention is not limited to the specific terms so used, and it should be understood that each specific term includes all its technical equivalents which operate in a similar manner to accomplish similar purpose.

Figure 4:
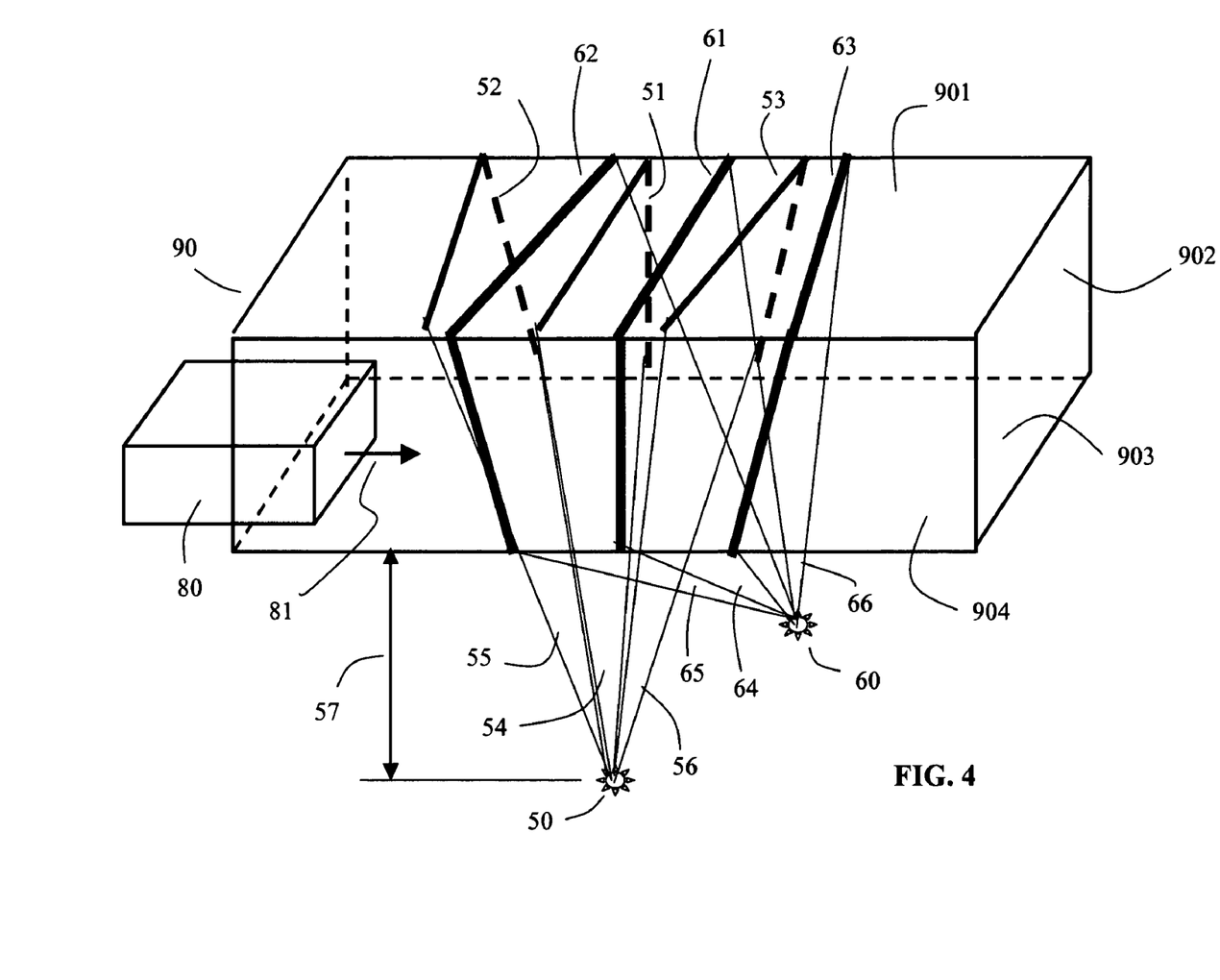
FIG. 4 shows a simplified sketch of the system as per one embodiment of this invention.

A simplified sketch of the preferred embodiment of the invention is shown in FIG. 4. An object or bag under inspection, 80, is moved in the direction 81, through a tunnel 90 comprising of walls 901, 902, 903 and 904. Two x-ray or radiation sources, a first radiation source 50 and a second radiation source 60 are shown located below and on the opposite sides of the tunnel 90. The x-ray source 50 emits a first radiation comprising of three radiation or fan beams 54, 55 and 56 that comprise a first set of beams. These radiation beams are incident on a first set of detectors 51, 52 and 53 and their paths of travel from the source to detectors constitute the first set of paths. Further, the beams 54, 55, and 56 are angularly spaced with respect to each other and are detected by the first set of detectors 51, 52 and 53 respectively.

As shown in FIG. 4, the location and orientation of second source 60 are such that its radiation is directed or oriented at an angle with respect to the first radiation from the first source 50. The three angularly spaced beams 64, 65 and 66 comprising the second radiation from the second source 60 are detected by a second set of detectors 61, 62 and 63 respectively. The radiation beams emitting from source 60 and incident on detectors 61, 62 and 63 constitute a second set of beams and their paths of travel from the source to detectors constitute a second set of paths. As shown in FIG. 4, the detectors are placed such that they receive radiation from their associated radiation source along paths that are oriented at different angles. The paths of radiation for detectors 51 and 61 make an angle of 90 degrees with the horizontal since their associated beams 54 and 64 are in the vertical planes. The direction of radiation beams for detectors 52, 53, 62 and 63 are slanted on either side of the vertical, the magnitude of the angles they make with the vertical may or may not be the same.

It should be noted that as shown in FIG. 4, the detectors belonging to the first set of detectors are interleaved with those in the second set of detectors. Likewise the first set of beams from the first source 50, are interleaved with the beams from the second source 60.

As shown in FIG. 4, each of the detectors 51, 52, 53, 61, 62, and 63 is like "L" shaped. Each of the "L" shaped detector has a horizontal part which lies on the top surface 901 of the tunnel 90, and a vertical part that is along the vertical side 902 or 904 of the tunnel as shown in FIG. 4. The vertical parts of 51, 52 and 53 are along the vertical wall 904 of the tunnel 90, and the vertical parts of 61, 62 and 63 are along the vertical wall 902 of the tunnel. As is well known to a person skilled in the art, each of the detectors is in fact an array of smaller detectors that are oriented towards the x-ray source that is emitting fan beams directed to these detectors. Also not shown to avoid the clutter in the drawings but well known to a person skilled in the art, are the conveyor belt, the rollers, the motors, various other mechanical details, the data acquisition electronics, the computer or image display system and other details required to build such a system. As is well known to a person skilled in the art, the relative translation between the said object and said radiation beams allows one to generate scanned pictures, further the use of multiple beams leads to a generation of multiple views of the object 80 from different angles or orientations, these scanned pictures or multiple views can then be analyzed in order to inspect the object.

Figure 5:
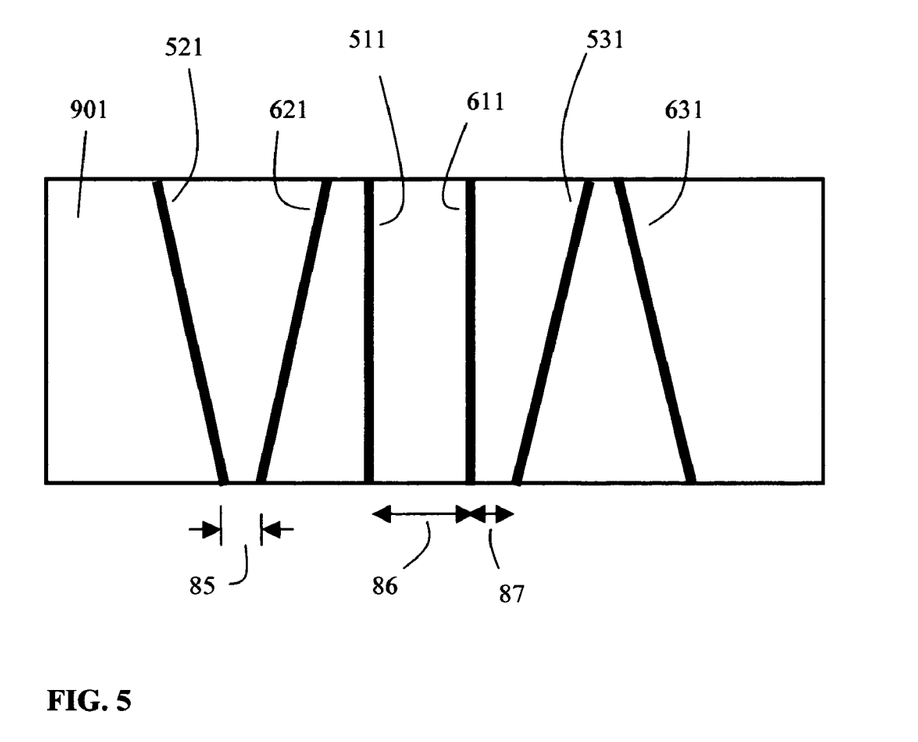
FIG. 5 shows the detector placement on the top of the tunnel for the embodiment shown in FIG. 4

The arrangement of the horizontal parts of the detectors is illustrated in FIG. 5. The horizontal parts of the detectors 51, 52 and 53 of FIG. 4 are shown as 511, 521 and 531 respectively in FIG. 5. Likewise the horizontal parts of detectors 61, 62 and 63 of FIG. 4 are shown as 611, 621 and 631 respectively in FIG. 5. It should be noted that for x-ray source 50, the arrangement of detectors 51, 52 and 53 in the first set of detectors is such that they are not parallel to each other. Likewise, for x-ray source 60, the arrangement of detectors 61, 62 and 63 in the second set of detectors is such that they are not parallel to each other. With reference to FIG. 5, it is seen that only 511 and 611 are parallel and perpendicular to the sides of the tunnel 90, these correspond to the central beams 54 and 64 that rise up in vertical planes from sources 50 and 60 respectively as shown in FIG. 4.

The angular width of the fan beams used in ordinary x-ray scanners is of the order of 60 degrees. With such a wide beam, the vertical height 57 of source 50 in FIG. 4 is usually in the range 10-15 inches below the belt. For such small distances of sources 50 and 60 below the belt, and the use of such a wide angled beams, the interleaving of beams from two sources as shown in FIG. 4, would lead to the intersection of some of the detectors 51, 52 and 53 with some of detectors 61, 62 and 63. Therefore in accordance with this invention, the distances 57 of source 50, and likewise of source 60, are increased such that for the chosen angles of the slant beams 55, 56 or 64, 66, the detectors do not intersect or are too close to each other. It should be noted that by adjusting or varying the distance 57, in essence the distance between the source 50 and its associated detectors 51, 52 and 53 is being changed. Therefore this distance between the source and detectors must not be too small to avoid the intersection of detectors for a two source system of FIG. 4. Adjusting the distance between sources and detectors, in such a way to prevent the intersection of detectors, leads to a compact multiview system with a small footprint.

Not shown for clarity of the drawings are the collimators associated with each of the detectors. As is well known to a person skilled in the art, these collimators are used to receive beams only from the desired direction, in this case the source the detector is associated with. Collimators are useful in that they eliminate the stray and back scattered x-rays coming from other than the direction of the source and hence lead to higher resolution images.

Figure 6:
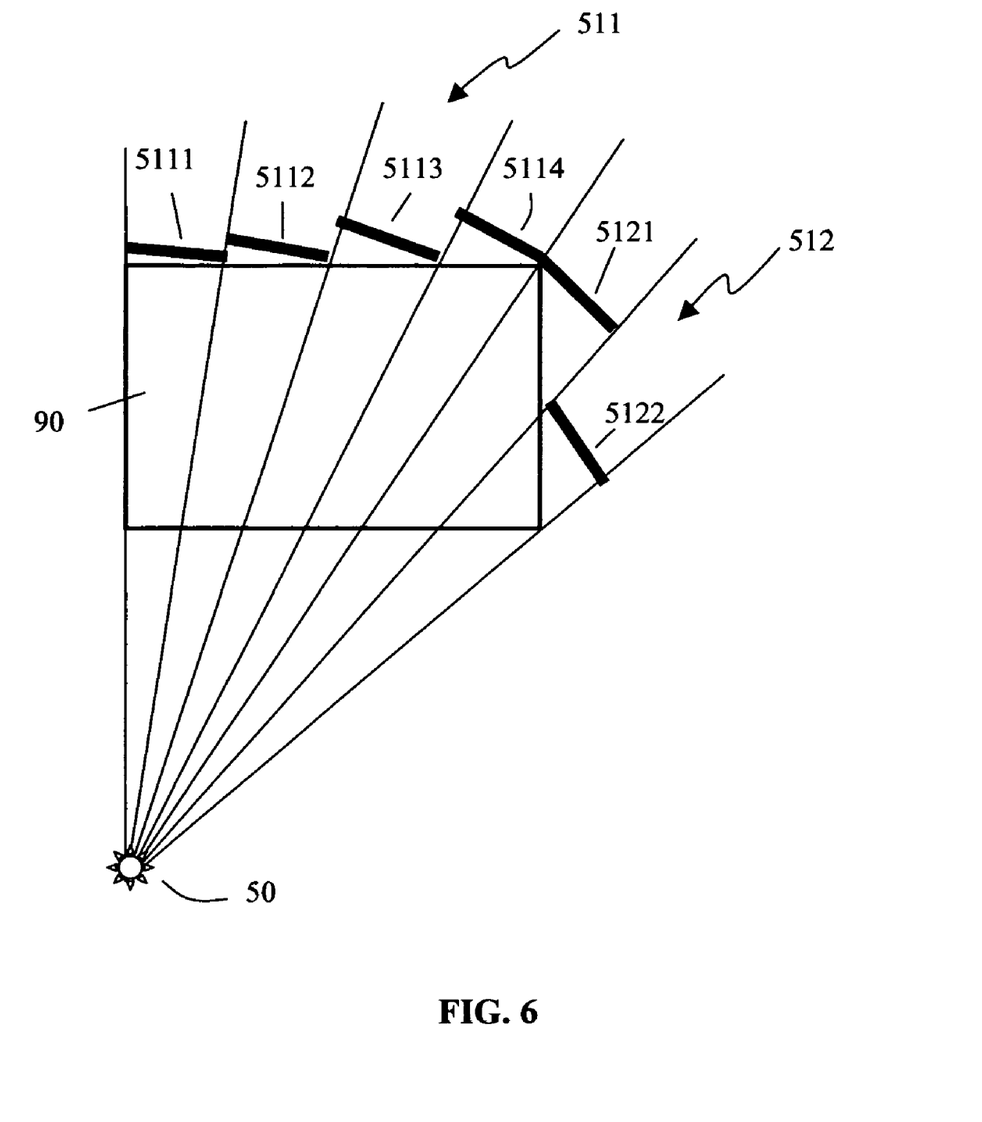
FIG. 6 shows the detector detail within any of the L shaped detector of FIG. 4.

The detail of any one detector is similar to that shown in FIG. 6 for the detector 51 associated with beam 54 coming from source 50 in FIG. 4. The horizontal part 511 of detector 51 is shown to be made of multiple smaller arrays, 5111, 5112, 5113 and 5114, each of which is oriented towards the source 50 to maximize the reception or the sensitivity of the detected signal. Likewise, the vertical part 512 of detector 51 has been shown to be comprising of multiple small sized arrays 5121 and 5122.

Also not shown for clarity of the drawings are the detector electronic boxes similar to the ones shown in FIG. 1 that go along with each of the detectors. These boxes house the preamplifiers and associated electronics that amplify and process the signal sensed by the detectors. The detector electronic boxes currently used are wide flat boxes as shown in FIG. 1 and FIG. 2. Their widths are usually in the range of 12 to 15 inches. However, the distances 85, 86 or 87 in FIG. 5 would only be a few inches for a small footprint scanner and this would make the system of FIG. 4 unrealizable if such wide detector electronic boxes were to be used. Therefore, this invention presents yet another novel feature of detector and electronics assembly that makes the detector electronic boxes narrow which leads to compact size of the overall system.

Figure 7:
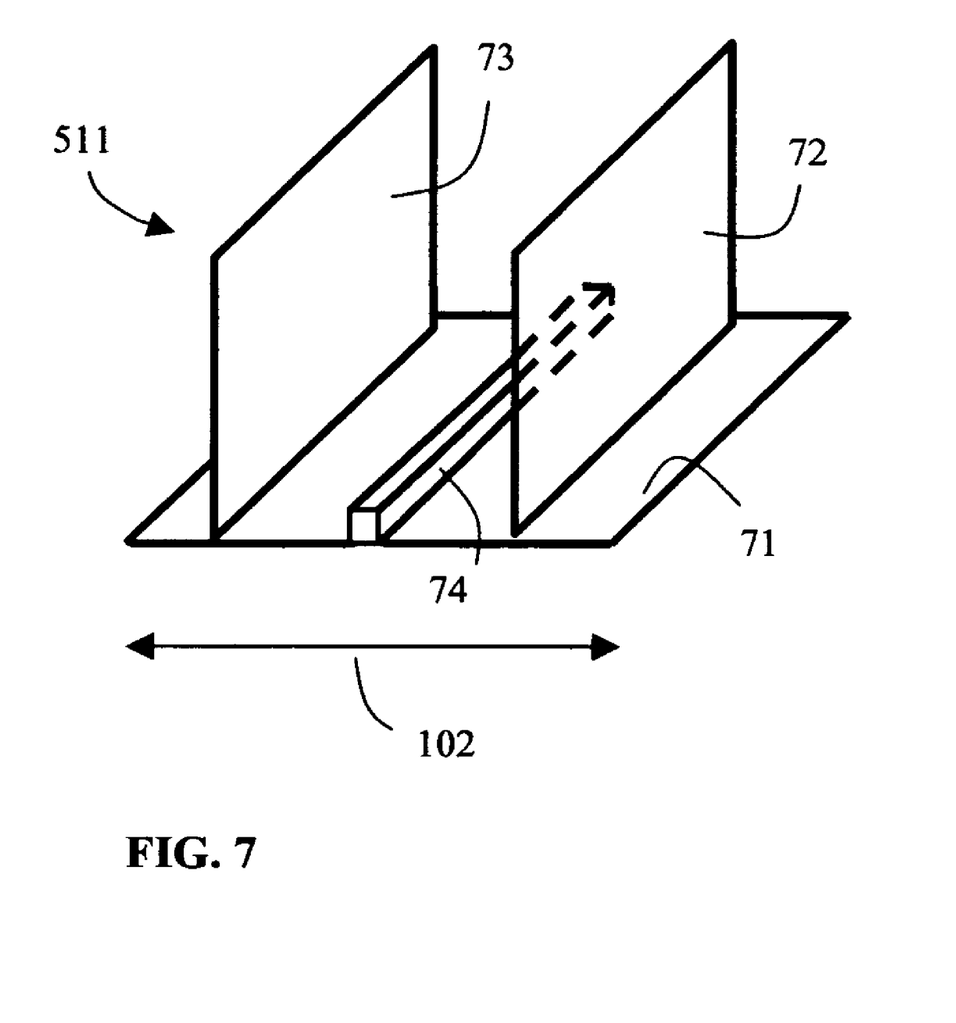
FIG. 7 shows the novel arrangement of detector and preamplifier electronics that reduces the width of the detector electronics box.

The novel arrangement of detector and preamplifier electronics, shown in FIG. 7, constitutes a novel detector device. In accordance with this invention, the novel detector device comprises of a detector 74 supported on a printed circuit board 71 hereafter called the detector board. The novel detector device further includes at least one preamplifier electronics board. These electronics boards are needed to amplify and further process the signal sensed by the detectors. In FIG. 7 are shown two preamplifier electronics boards, 72 and 73. These boards are placed vertically over the detector board 71. This vertical arrangement of electronics boards over the detector board leads to a very small width dimension 102 of only about a couple of inches or so compared to the 12 to 15 inches of the usual boxes currently being used. The narrow width of the detector electronic boxes thus achieved by this invention, therefore allows the detectors to be placed in close proximity to one another. This allows one to realize the system where the detectors are placed according to FIG. 4 and FIG. 5 which in turn leads to a very compact system of high resolution. It should be noted that in the novel detector device of FIG. 7, two electronic cards have been shown, but only one or more than two electronic cards can be used. Further, the electronics and detector can be mounted on one flexible board instead and the board bent at right angles so as to make the detectors at right angle to the electronics. Alternatively, the detector and electronics could be mounted on one rigid board such that the plane of electronics is vertical or parallel to the incident radiation beam and the detectors are held by a means such that the detectors are oriented towards the incident radiation beam. It should be noted that the main feature of the novelty is that electronics is arranged or assembled over a plane that is essentially parallel to the incident radiation beam where as in the prior art they were arranged orthogonal or at right angles to the incident radiation. It is however not necessary that the electronics be parallel to or make a zero degree angle to the incident radiation beam, it could make a 45 degree angle to the incident radiation beam thereby realizing half the shrinkage in width of the detector electronic box as this may be acceptable in some situations. This is the same as saying that electronic boards or the plane of electronics should be at an angle substantially different from 90 degrees to the incident radiation beam, the desired angle being zero.

It should be noted that it is not necessary to house the detectors in boxes that are arranged in "L" shaped configuration. Instead of two detector electronic boxes, three or more boxes can be used and arranging them such that the detectors are oriented towards the source they are detecting the radiation from.

Figure 8:
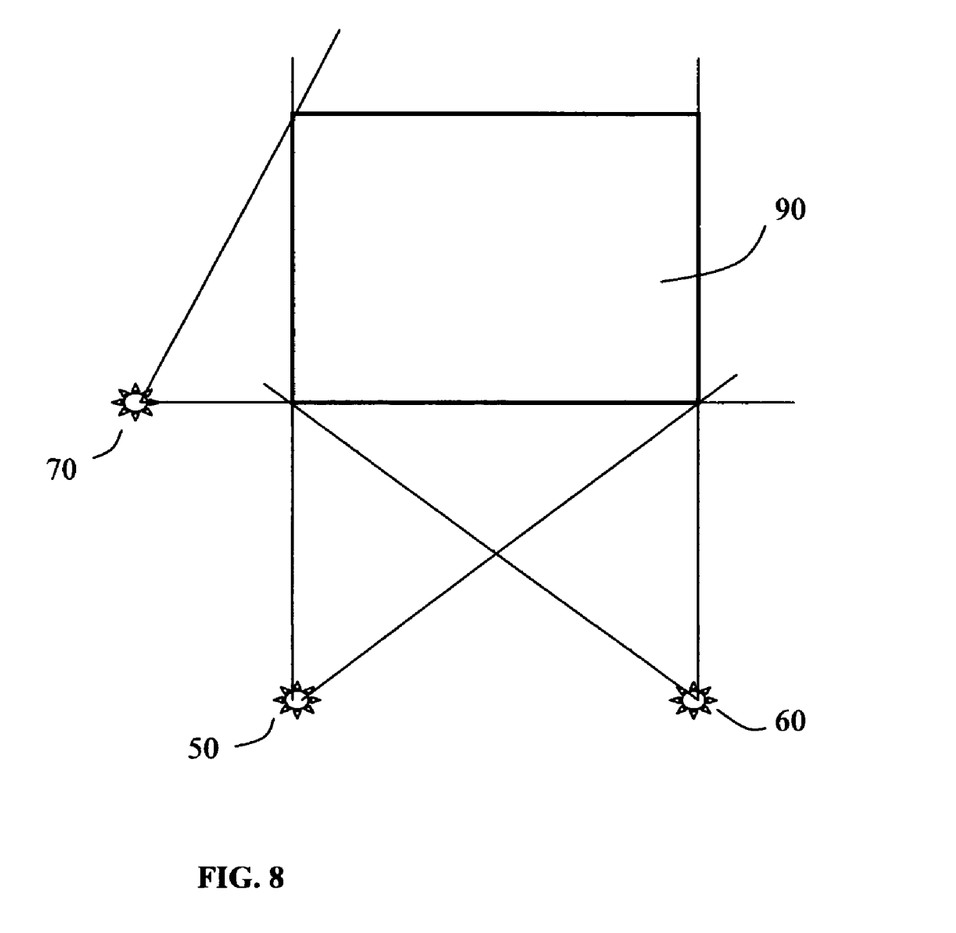
FIG. 8 shows the location of three x-ray sources in an alternate embodiment of the invention.

In the preceding discussion, only two sources each with three beams have been used. However, as would be apparent to a person skilled in the art, several variations are possible. One such alternate embodiment uses a third source 70 shown in the end view of the tunnel in FIG. 8. As shown, the direction of radiation of the third source is substantially horizontal. The location of the third source can be different from that shown, what is important is that its radiation is directed such that it makes a substantial angle to both the radiation from the first source 50 and that from the second source 60. Further, instead of 3 beams per source, fewer or more beams can be used.

As is well known to a person skilled in the art the data, obtained from the various detectors as described in this invention, leads to generation of views of the object from different angles. These views can be analyzed or combined including the method of laminography or tomography or computer reconstruction to analyze the object under inspection.

The foregoing description of the invention and its embodiments should be considered as illustrative only of the concept and principles of the invention. The invention may be configured in a variety of ways, shapes and sizes and is not limited to the description above. Numerous applications of the present invention will readily occur to those skilled in the art. Therefore, it is desired that the scope of the present invention not be limited by the description above but by the claims presented herein.

The invention claimed is:

1. A method of inspecting an object comprising the steps of:
    using at least a first radiation source generating a first radiation;
    positioning a plurality of radiation detectors comprising a first set of detectors such that said first radiation is incident on each detector along a first set of paths that are oriented at different angles;
    generating a second radiation using a second radiation source;
    orienting said second radiation such that it is at an angle to said first radiation;
    positioning a plurality of radiation detectors comprising a second set of detectors such that said second radiation is incident on each detector along a second set of paths that are oriented at different angles;
    further interleaving detectors in said first set of detectors with detectors in said second set of detectors;
    interposing said object between said first source and said first set of detectors, and between said second source and said second set of detectors;
    translating said object relative to said first and second radiations; and
    analyzing data received from said first set of detectors and said second set of detectors.

2. The method of claim 1 wherein:
    positioning of plurality of detectors in said first set of detectors is such that none of said detectors are parallel to each other; and
    positioning of plurality of detectors in said second set of detectors is such that none of said detectors are parallel to each other.

3. The method of claim 2 wherein the distances from said first source to said first set of detectors and that from said second source to said second set of detectors are adjusted such that the detectors in said first set of detectors do not intersect with the detectors in said second set of detectors.

4. The method of claim 1 wherein each detector in said first set of detectors and said second set of detectors, further includes at least one electronics board arranged at an angle to incident radiation that is substantially different from ninety degrees.

5. The method of claim 1 further comprising the steps of:
generating a third radiation using a third radiation source;
orienting said third radiation such that it is at an angle to said first radiation and to said second radiation; and
positioning a third set of detectors comprising of at least one detector oriented towards said third radiation from said third source.

6. An apparatus for inspecting an object comprising of:
a first radiation source generating a first radiation;
a plurality of radiation detectors comprising a first set of detectors positioned such that said first radiation is incident on said detectors along a first set of paths that are oriented at different angles;
a second radiation source generating a second radiation oriented such that said second radiation is at an angle to said first radiation;
a plurality of radiation detectors comprising a second set of detectors positioned such that said second radiation is incident on said detectors along a second set of paths that are oriented at different angles;
further, the arrangement of said detectors is such that detectors in said first set of detectors are interleaved with detectors in said second set of detectors;
a means to interpose said object between said first source and said first set of detectors, and between said second source and said second set of detectors;
a means to translate object relative to said first and second radiations; and
a means to analyze data received from said first set of detectors and said second set of detectors.

7. The apparatus of claim 6 wherein:
said plurality of detectors comprising said first set of detectors are so arranged that none of said detectors are parallel to each other; and
said plurality of detectors comprising said second set of detectors are so arranged that none of said detectors are parallel to each other.

8. The apparatus of claim 7 wherein the distances from said first source to said first set of detectors and that from said second source to said second set of detectors are such that the detectors in said first set of detectors do not intersect with the detectors in said second set of detectors.

9. The apparatus of claim 6 wherein each detector, in said first set of detectors and said second set of detectors, further includes one at least one electronics board arranged at an angle to incident radiation that is substantially different from ninety degrees.

10. The apparatus of claim 6 further comprising of:
a third radiation generating a third radiation source oriented such that said third radiation is at an angle to both said first radiation and said second radiation; and
a third set of detectors comprising of at least one detector oriented towards said third source.

11. A radiation detector device to detect incident radiation, said detector device having a width dimension that is along a direction perpendicular to the path of said incident radiation, said detector device comprising of:
at least one detector oriented so as to detect said incident radiation; and
at least one electronics board arranged at an angle to said incident radiation that is substantially different from ninety degrees such that said width dimension of said detector device is reduced.

* * * * *